(12) United States Patent
Shabudin

(10) Patent No.: US 11,253,654 B2
(45) Date of Patent: Feb. 22, 2022

(54) INJECTION DEVICES

(71) Applicant: Owen Mumford Limited, Oxford (GB)

(72) Inventor: Tahir Shabudin, Oxford (GB)

(73) Assignee: Owen Mumford Limited, Oxford (GB)

( * ) Notice: Subject to any disclaimer, the term of this patent is extended or adjusted under 35 U.S.C. 154(b) by 111 days.

(21) Appl. No.: 16/338,215

(22) PCT Filed: Oct. 2, 2017

(86) PCT No.: PCT/GB2017/052956
§ 371 (c)(1),
(2) Date: Mar. 29, 2019

(87) PCT Pub. No.: WO2018/060745
PCT Pub. Date: Apr. 5, 2018

(65) Prior Publication Data
US 2020/0030539 A1 Jan. 30, 2020

(30) Foreign Application Priority Data
Sep. 30, 2016 (GB) .................................... 1616712

(51) Int. Cl.
*A61M 5/315* (2006.01)
*A61M 5/20* (2006.01)
(52) U.S. Cl.
CPC ........ *A61M 5/3157* (2013.01); *A61M 5/2033* (2013.01); *A61M 5/3158* (2013.01);
(Continued)
(58) Field of Classification Search
CPC .............. A61M 5/3157; A61M 5/2033; A61M 2005/31518; A61M 2205/43;
(Continued)

(56) References Cited

U.S. PATENT DOCUMENTS 3,660,037 A 5/1972 Sokol
5,591,188 A 1/1997 Waisman
(Continued)

FOREIGN PATENT DOCUMENTS

CN 103492001 A 1/2014
CN 105451792 A 3/2016
(Continued)

OTHER PUBLICATIONS

International Search Report and Written Opinion, International Application No. PCT/GB2017/052956, dated Jan. 4, 2018, 18 pages.
(Continued)

*Primary Examiner* — Bhisma Mehta
*Assistant Examiner* — Neeraja Gollamudi
(74) *Attorney, Agent, or Firm* — Quarles & Brady LLP

(57) ABSTRACT

An injection device (1) for the delivery of medicament has an indicator (50) for providing an end of dose indication. The device comprises a housing (10), an extendable plunger (40), an actuation mechanism (30), a trigger arrangement (15), and an indicator (50). The extendable plunger (40) comprises a leading portion (42) and a trailing portion (48) configured to allow the plunger (40) to extend from an initial length to a maximum extended length, the plunger portions ((42),48) being slidably mounted within the housing (10). The actuation mechanism (30) is configured to move the leading portion (42) of the plunger (40) forwardly relative to a syringe (20) so as to express medicament from the syringe (20). The trigger arrangement (15) is moveable in use to release the actuation mechanism (30). The indicator (50) is responsive to the forward movement of the plunger (40) and is configured to provide an audible and/or tactile and/or visual indication of the end of dose when the plunger (40) reaches or approaches its forwardmost position.

18 Claims, 7 Drawing Sheets

(52) U.S. Cl.
CPC ............. *A61M 2005/31518* (2013.01); *A61M 2205/43* (2013.01); *A61M 2205/581* (2013.01); *A61M 2205/582* (2013.01); *A61M 2205/583* (2013.01)

(58) Field of Classification Search
CPC ...... A61M 2205/581; A61M 2205/582; A61M 2205/583
See application file for complete search history.

(56) References Cited

U.S. PATENT DOCUMENTS

| | | | |
|---|---|---|---|
| 2004/0210199 A1* | 10/2004 | Atterbury | G01D 5/25 604/224 |
| 2013/0245604 A1* | 9/2013 | Kouyoumjian | A61M 5/1408 604/506 |
| 2013/0324939 A1 | 12/2013 | Brereton et al. | |
| 2014/0330216 A1 | 11/2014 | Weaver et al. | |
| 2015/0196713 A1 | 7/2015 | Karlsson et al. | |
| 2016/0058955 A1 | 3/2016 | Olson et al. | |

FOREIGN PATENT DOCUMENTS

| | | | |
|---|---|---|---|
| CN | 105492048 A | 4/2016 | |
| CN | 105854129 A | 8/2016 | |
| EP | 2583705 A1 | 4/2013 | |
| WO | 2010035056 A1 | 4/2010 | |
| WO | 2015187913 A1 | 12/2015 | |
| WO | 2016027096 A1 | 2/2016 | |
| WO | WO-2016027096 A1 * | 2/2016 | .......... A61M 5/3129 |

OTHER PUBLICATIONS

Search Report, UK Application No. GB1616709.0, dated Feb. 28, 2017, 4 pages.
First Office Action from corresponding Chinese Patent Application No. 2017800608682, dated Dec. 9, 2020 (16 pages).

\* cited by examiner

Assembled state

After actuation

End of dose

# INJECTION DEVICES

CROSS-REFERENCE TO RELATED APPLICATIONS

This application represents the U.S. National Stage of International Application No. PCT/GB2017/052956 filed Oct. 2, 2017, which is based on, claims priority to, and incorporates herein by reference in its entirety, British Patent Application Serial No. GB 1616712.4, filed Sep. 30, 2016, and entitled, "Injection Devices."

FIELD OF THE INVENTION

This invention relates to injection devices, particularly injection devices including an end of dose indication.

BACKGROUND OF THE INVENTION

Injection devices are used for the convenient administration of medicaments. For example, auto injectors may be used for providing a single metered dose of a medicament, such as Epinephrine, in an emergency or for providing regular metered doses of a medicament, such as insulin. An example of one such injection device is shown in the applicant's co-pending application PCT/GB2011/051950. Such injectors typically comprise a housing within which is housed (or defined) a syringe or cartridge containing medicament. The housing generally includes an actuation mechanism which may be of any convenient form and is arranged to move a plunger between an initial rearward, position and, a forward, delivery position so as to express medicament from the syringe.

It is known to provide such injection devices with an activation indicator which provides one or more of a visual, tactile or audible indication of the firing of the injector actuation mechanism. In particular since the delivery of a desired dose of medicament may take a certain amount of time after the user activates the injector (particularly for example, with high viscosity drugs or small needle diameters) it is useful to provide an injection complete indication. The term "Injection Complete" (or "injection completion") is used to refer to a condition in which a satisfactory delivery of the medicament has been achieved. An example of an injection device with an activation indicator is shown in the applicant's co-pending application PCT/GB2015/052424.

It is desirable for auto injectors to be of a compact form so that they can be carried around and used unobtrusively (typically such auto injectors are provided in a pen injector type form). Further compact injectors may be simple to manufacture, assemble and use with consequent savings in manufacturing and assembly costs, and a lower environmental impact. Accordingly, any activation indicator provided within the injector must be of compact form and not significantly impact the overall size of the injection device.

Embodiments of the present invention are intended to improve on the existing injection devices described above.

SUMMARY OF THE INVENTION

Accordingly, in one aspect, the present invention provides an injection device for the delivery of medicament and having an indicator for providing an end of dose indication, the device comprising:
 a housing;
 an extendable plunger comprising a leading portion and a trailing portion configured to allow the plunger to extend from an initial length to a maximum extended length, the plunger portions being slidably mounted within the housing;
 an actuation mechanism configured to move the leading portion of the plunger forwardly relative to a syringe so as to express medicament from the syringe;
 a trigger arrangement moveable in use to release the actuation mechanism; and
 an indicator responsive to the forward movement of the plunger and configured to provide an audible and/or tactile indication of the end of dose when the plunger reaches or approaches its forwardmost position;
 wherein the indicator is biased towards the indicating position and the trailing portion of the plunger is arranged to hold the indicator against said bias;
 the device being characterised in that the indicator is configured to move forward relative to at least the trailing portion of the plunger in response to activation movement of the trigger arrangement;
 the trailing portion is arranged to move in the forward direction in response to the extendable plunger reaching its maximum extension; and
 the indicator is arranged to be responsive to the forward movement of the trailing portion.

Typically, the indicator may be arranged to provide an injection completion indication, such as an end of dose indication, and as such may be configured to be responsive to arrival of the plunger at or near its fowardmost position (at which position the medicament will have been fully dispensed).

In the context of the present invention, the rearward portion of the injection device is defined as the non-patient end of the device, which is the end of the injector assembly (or components thereof) which, in use, is furthest from a delivery needle end of the injector (i.e. the end which is pointed away from the skin). The forward portion of the injection device is defined as the patient end of the device, which is the end of the injector assembly (or components thereof) which, in use, is closest to the delivery needle delivery end of the injector (i.e. the end which is pointed at the skin).

"Forward" and "rearward" will, likewise, be understood to refer to the directions orientated towards the front and rear of the injector assembly.

Components which are moved forward or forwardly, are moved towards the patient end of the injection device; and components with features provided at a forward or forwardmost end, are provided at the end of the component closest to the patient end of the device. Components which are moved rearward or rearwardly, are moved towards the non-patient end of the injection device; and components with features provided at, or proximal to, a rearward or rearwardmost end, are provided at, or proximal to, the end of the component closest to the non-patient end of the device.

It will be appreciated that the forward direction is generally the actuation direction of the device (although in some devices there may be some steps of the actuation, for example a needle withdrawal, which are in the rearward direction). The term "leading" is used herein to conveniently refer to the section(s) of the plunger which lead during actuation movement, for example in that they either move forward first, or sequentially, or move forward to the forwardmost position. Likewise "trailing" will be understood to refer to the section(s) which are rearwardmost during or after actuation.

The extendable plunger may comprise interconnected sections which are relatively moveable in the axial direction such that the overall axial length of the plunger may be extended. The plunger may be expanded between a collapsed configuration in which the axial length of the plunger is at a minimum, and an expanded configuration in which the length of the plunger is extended. The interconnection between the sections may allow relative axial movement between the sections but may also provide a stop or limit to the relative axial movement between the sections so as to limit the movement beyond a predetermined extent. The stop or limit to the relative axial movement defines the maximum extension of the plunger.

Release of the indicator (in response to the forward movement of the trailing portion of the plunger) may be arranged to enable said indicator to move under its bias. The movement of the indicator may be arranged to create a kinetic impact resulting in an audible and/or tactile indication. For example, the indicator may strike a percussive surface which may, for example, be associated with the housing of the injection device. Alternatively, the indicator may include opposing members which are arranged to strike one another to provide the kinetic impact.

The indicator may comprise a resilient member, preferably one or more resilient members. The, or each, resilient member may be held in a stressed position (i.e. against its own bias) when the plunger is in its rearward position. For example, the indicator may comprise a spring. The spring may be under compression when the trailing portion is in its rearward position. The spring may be configured to expand in response to the forward movement of the trailing portion, such that the indicator is moved to the indicating position to create the kinetic impact indicating the end of dose.

The forward movement of the indicator relative to at least the trailing portion of the plunger in response to activation movement of the trigger arrangement may increase the mechanical coupling between the indicator and the trailing portion of the plunger holding the indicator in a stressed position.

The leading portion may comprise an internal abutment surface proximal to its rearward end. For example, the internal abutment surface may be provided by a portion of reduced internal diameter proximal to its rearward end, creating a stepped profile. The trailing portion may comprise a corresponding stop portion proximal to its forward end. For example, the stop portion may be defined by a portion of increased diameter.

In embodiments, the stop portion of the trailing portion may be configured to co-operate with the internal abutment surface of the leading portion when the plunger reaches or approaches maximum extension. The trailing portion may be arranged to move forward in response to the co-operation between the portion of reduced internal diameter, or the internal abutment surface, of the leading portion, and the portion of increased diameter, or stop portion, of the trailing portion. The forward movement of the trailing portion may release the indicator to create the kinetic impact.

The indicator may comprise an aperture. The aperture may extend generally longitudinally through the indicator. The trailing portion may be receivable along the length of the longitudinal aperture. The aperture may comprise a radially inwardly extending portion, for example a lip, extending around at least a portion of the aperture. For example, the radially inwardly extending portion may extend around at least a portion of the forwardmost end of the aperture. The radially inwardly extending portion may be configured to engage the trailing portion in response to activation of the injection device.

The trailing portion may comprise a recess for receiving the radially inwardly extending portion proximal to its rearward end. The recess may be defined by, for example a portion of reduced diameter, such as a neck. In such embodiments, the radially inwardly extending portion may be configured to engage the neck of the trailing portion in response to activation of the injection device. Advantageously, interaction between the radially inwardly extending portion and the neck may provide an increased resistance, or increased mechanical coupling, to the forward movement of the trailing portion compared to embodiments with no such radially inwardly extending portion or neck. Such increased resistance can help to mitigate the risk that the trailing portion will move forward prematurely, thus incorrectly indicating the end of dose. In turn, this can help to minimise the risk that the user will terminate the delivery of medicament prematurely due to a false indication, and thus receive an underdose of medicament.

The indicator may comprise a shuttle. The shuttle may be arranged for generally transverse movement under the indicator bias. For example, the shuttle may be disposed in a generally transverse passageway. The transverse passageway may, for example, be formed in the housing (for example, within a trigger button) of the injection device. The shuttle may be moveable along the length of the transverse passageway. The indication position of the shuttle may be at, or proximal to, one end of the passageway. The shuttle may be biased towards the indicating position along the length of the transverse passageway.

The plunger may be arranged, in its rearward position, to lock or hold the shuttle against the bias in a position which is spaced away from the end of the passageway.

The shuttle may comprise a non-circular cross-section, particularly when viewed along an axial plane of the injection device. For example, the shuttle may comprise a substantially rectangular or square cross-section when viewed along an axial plane of the injection device. Advantageously, a rectangular or square cross-section may help to mitigate any rotation of the shuttle within the passageway, and may also help to keep the shuttle centred within the passageway.

At least one outer surface of the shuttle, for example at least one side surface, may comprise a stepped profile. A side surface is defined as being parallel to the longitudinal length of the aperture. At least one inner surface of the transverse passageway may comprise a corresponding rib, or lip, which is configured to co-operate with the stepped profile to support the shuttle within the passageway. The stepped profile and corresponding rib may interact in only one configuration, which may be advantageous during assembly to help ensure the shuttle is mounted within the passageway in the correct orientation. The rearwardmost outer surface of the shuttle may comprise a groove extending across the width of the shuttle. The groove may help to ensure that the shuttle is mounted within the passageway in the correct orientation, particularly during mechanical assembly of the injection device.

The extendable plunger may be a telescopic plunger. Telescopic as used herein is intended to refer to elongate interconnected sections which are relatively moveable in the axial direction such that the overall axial length of the plunger may be extended (for example the sections may slide relative to one another). In other words, the telescopic sections enable the plunger to be expanded between a collapsed (or nested) configuration in which the sections substantially overlap and an expanded configuration in which the plunger is extended to a maximum axial length. The interconnection between the sections may allow relative axial movement between the sections but may provide a stop or limit to the relative axial movement between the sections (so as to limit the movement beyond a predetermined extent and maintain the integrity of the plunger).

In the context of the invention the sequential movement of the plunger sections should be understood to mean that each of the sections moves during the operation sequence of the device. The particular order of movement of the sections may depend upon the particular embodiment of the invention. The skilled person will appreciate that during the actuation movement of the plunger the movement/expansion of the plunger sections may involve a degree of compound movement. For example at least some sections of the plunger may move together for at least a portion of the activation. In other words, through the full actuation movement the plunger sections may each move relative to the housing (to provide the required forward movement of the syringe plunger) and may move relative to one another (to provide the expansion of the plunger) but the particular order of the movement during any portion of the activation is not considered essential to the invention.

Advantageously, the provision of a telescopic plunger may provide a convenient and compact means of activating the indicator. In particular, it will be appreciated that the length of the telescopic plunger can be easily adjusted in order to provide the desired timing of the indicator response when producing an injection device in accordance with an embodiment of the invention.

In some embodiments, the trailing portion of the plunger may be at least partially surrounded by, for example, at least one of the other telescopic sections. Thus, one or more of the leading portion(s) may be the section(s) having the greatest radial width so as to reduce the stressed position of the resilient member gradually or in stages during extension of the telescopic plunger.

The actuation mechanism may comprise a drive source and a latch arranged to hold the plunger in a rearward position against the drive source. As such, the rearward position of the plunger may be a cocked position of the actuation mechanism. The trigger arrangement may comprise a trigger (which may be associated with the housing) arranged to release the latch. On release of the latch, the plunger is able to move forward under the influence of the drive source. Thus, the drive source may act to expand the plunger and move the leading portion (or alternatively sequentially move each of the telescopic sections) forwardly within the housing. The trigger may be further arranged to move the indicator forward relative to at least the trailing portion of the plunger, such that the neck of the trailing portion engages with the radially inwardly extending portion of the aperture.

In some embodiments the drive source may simply be a spring such as a compression spring. In a particular embodiment the actuation mechanism comprises an intermediate drive member. The drive source may, therefore, comprise a first drive spring disposed between the intermediate drive member and the housing (or a part associated therewith) and a second compression spring disposed between the intermediate drive member and the plunger. In such an arrangement, upon release of the latch the drive springs urge the intermediate drive member and plunger forwardly (and may act in a compound motion). The second compression spring may act upon a rearward facing flange surface formed at the forwardmost end of the plunger.

The leading portion of the plunger may comprise an external abutment surface configured to be releasably engaged by the latch of the actuation mechanism. The external abutment surface may be formed at the rearward end of the leading portion of the plunger. The external abutment surface may, for example, be formed at the rearward end of the leading portion. When the plunger is in its fully collapsed configuration, the further abutment surface may be at, or proximal to, the rearward end of the plunger.

Whilst the invention has been described above, it extends to any inventive combination set out above, or in the following description or drawings.

BRIEF DESCRIPTION OF THE DRAWINGS

The invention may be performed in various ways, and embodiments thereof will now be described by way of example only, with reference being made to the accompanying drawings, in which.

DETAILED DESCRIPTION OF EMBODIMENTS

For convenience the preferred embodiment is shown in an injector device substantially of the type disclosed in the applicants co-pending International Patent Application No. PCT/GB2011/051950 (the contents of which is incorporated herein by reference). It will however be appreciated that the invention is not limited to such an arrangement and may be used in injectors having other actuation arrangements.

Figure 1:
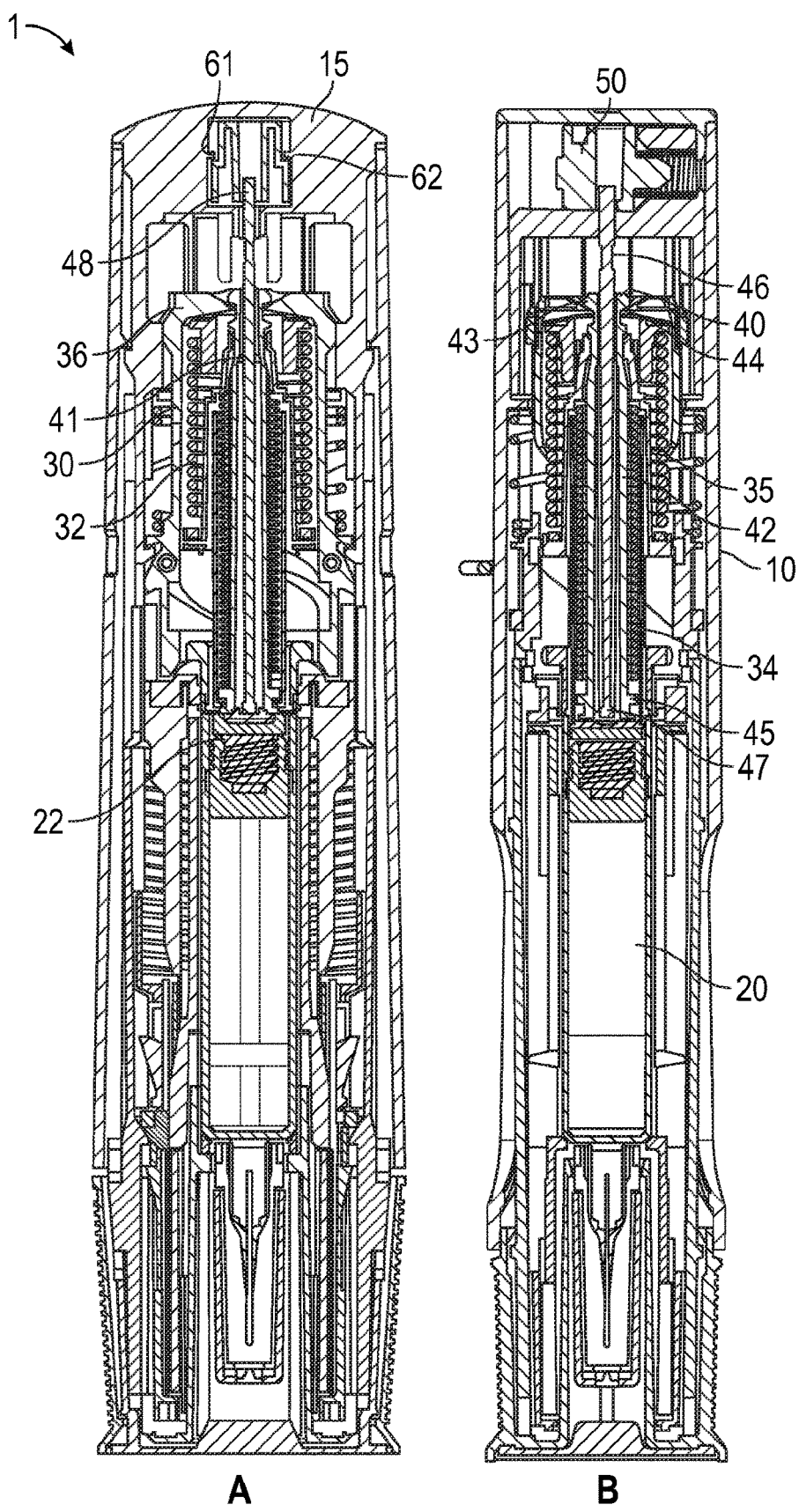
FIG. 1 shows two sectional views A and B, offset by a 90 degree rotation along the longitudinal axis, of an injection device in accordance with the present invention.
Figure 2:
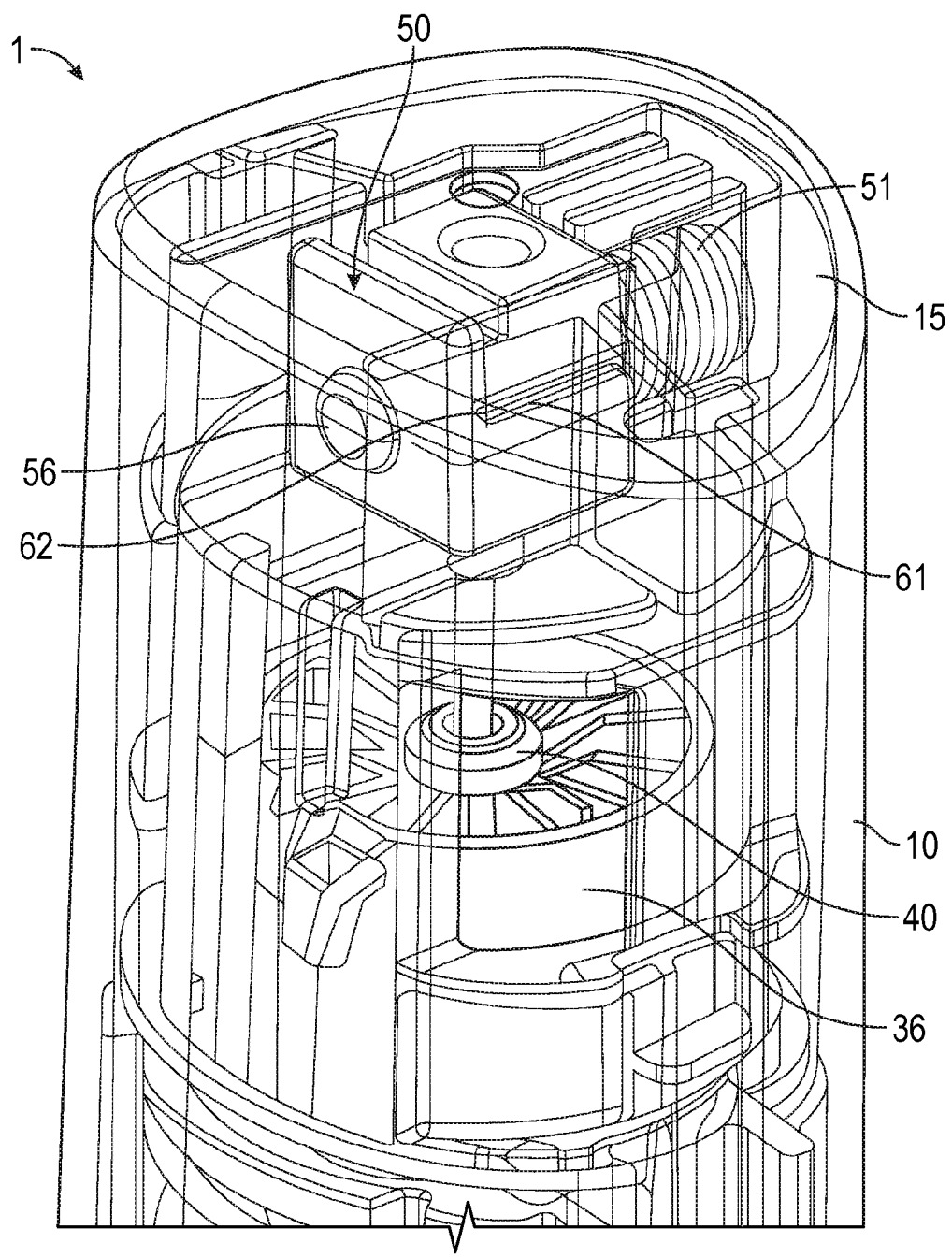
FIG. 2 is a three-dimensional view of the rear section of an injection device in accordance with the present invention.
Figure 3:
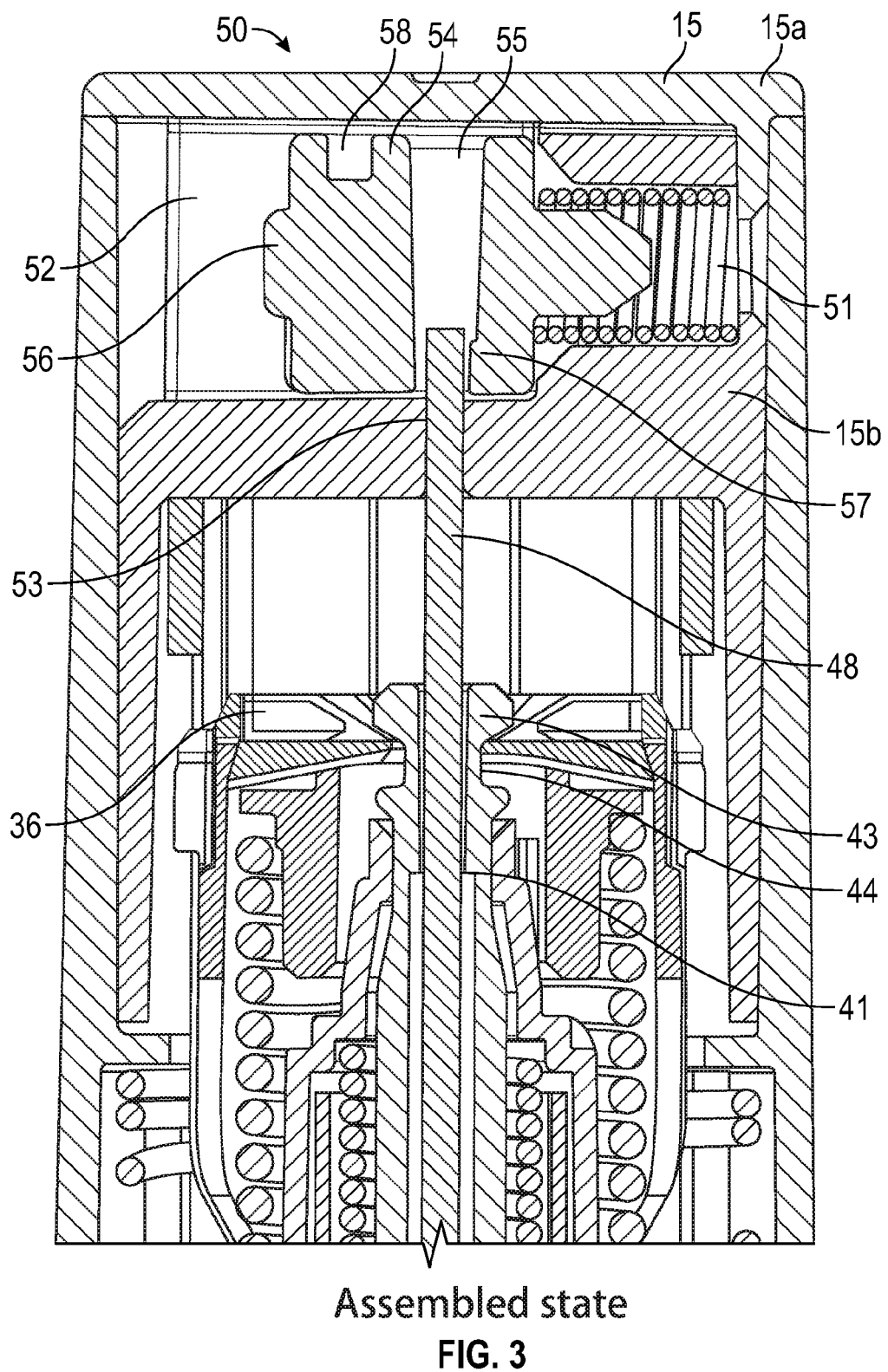
FIG. 3 is a sectional view of the rear of an injection device showing the position of the indicator before activation.

FIGS. 1-3 show an injection device 1 comprising a housing 10 having a generally elongate and cylindrical form within which is housed a syringe 20. The rear portion of housing 10 includes an actuation mechanism 30 which may be of any convenient form. The forward portion of housing 10 encloses the syringe 20 and the needle at the forward end of the syringe 20.

The actuation mechanism 30 is arranged to move a plunger 40 between an initial rearward position, as shown in FIGS. 1-3, and a forward delivery position such that the plunger 40 may express a dose of medicament from the syringe 20 by moving the bung or piston 22 of the syringe 20 forward within the syringe body. The actuation mechanism 30 is of the type which initially moves the syringe 20 forward from within the housing 10 such that the needle of the syringe may automatically penetrate the skin and then subsequently continues to move the plunger relative to the syringe to express the entire dose of medicament from within the syringe 20. As mentioned above, the present invention is not limited to any particular actuation mechanism and it will, therefore, be appreciated that other injector arrangements are known in which the needle protrudes from the housing prior to firing such that it is manually inserted into the skin (and the syringe may be fixed relative to the housing). The actuation mechanism 30 includes a drive source in the form of at least one compression spring 32, 34 for urging the plunger 40 and a latch 36 which initially holds the plunger 40 in its rearward position against the force of the spring 32, 34. The rearward end of the plunger 40 is provided with an enlarged head 43 which is positioned rearwardly of a neck defining an abutment surface 44 for engagement with the latch 36 of the actuation mechanism 30. A trigger 15 is provided associated with the housing 10 and is arranged in use to release the plunger 40 from the latch 36 to free it for forward movement.

The injection device 1 includes an actuation mechanism 30 of the type which includes a first drive spring 32, which extends between an intermediate member 35 and a surface associated with the housing 10, and a second drive spring 34, which extends between the intermediate member 35 and a flange 45 having a rearward facing abutment surface, for receiving the spring 34 which is formed at the forward end of the plunger 40. The flange 45 has a rearward facing abutment surface for receiving the spring 34.

Figure 4:
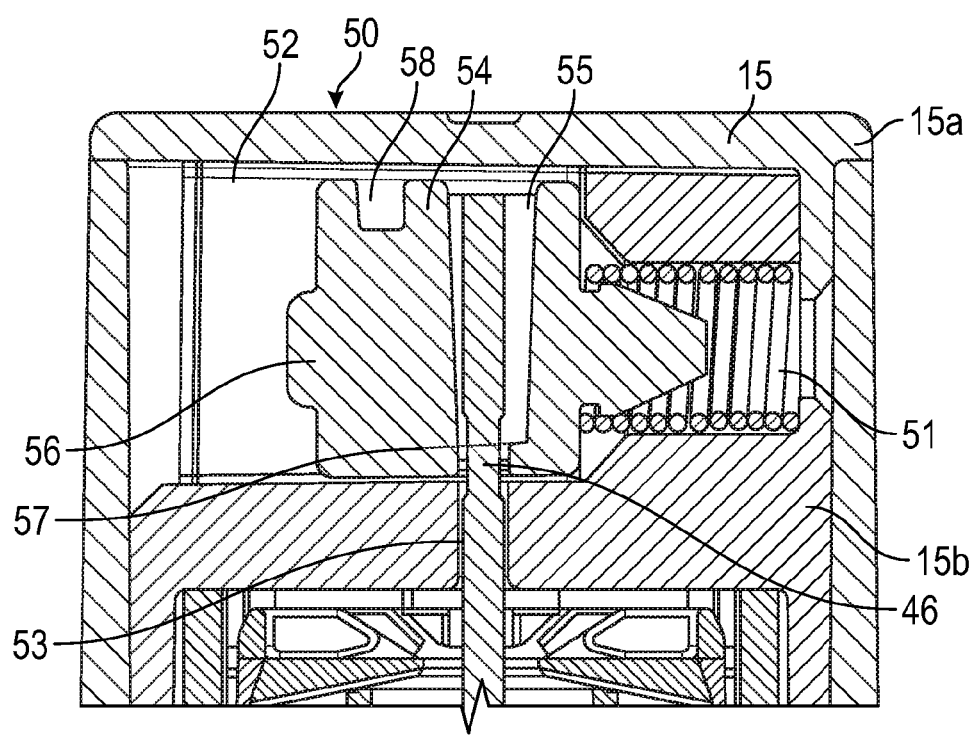
FIG. 4 is a sectional view of the rear of an injection device showing the position of the indicator after activation.
Figure 5:
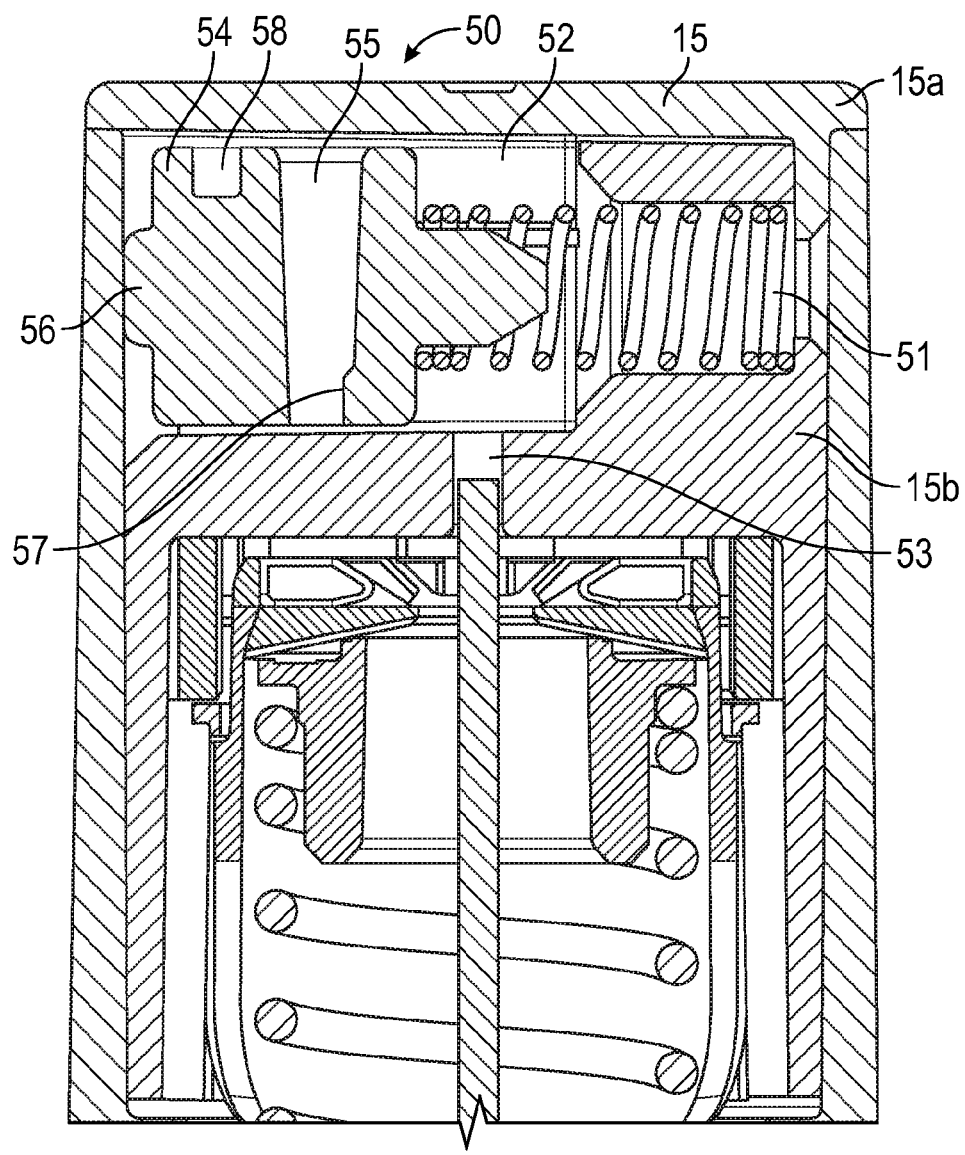
FIG. 5 is a sectional view of the rear of an injection device showing the indicator in the indicating position.

FIGS. 1-3 show the injection device 1 in a position prior to firing, such as before the injection device has been activated. In use, the injection device 1 is placed against a user's skin, and the housing 10 is moved forward, exposing the trigger 15. The trigger 15 is then activated, by depressing the trigger, thus activating the injection device. FIGS. 4-5 show the trigger 15 after it has been depressed, causing the head 43 of the plunger 40 to be released from the latch 36.

The plunger 40 comprises a trailing portion 48 positioned within a leading portion 42. In this embodiment, the plunger 40 is telescopic, and the telescopic plunger portions 42, 48 are generally concentric.

The trailing portion 48 comprises a recess defined by a portion of reduced diameter, such as a neck 46, proximal to its rearmost end, and a portion of increased diameter, or a stop 47, proximal to its forwardmost end. The leading portion 42 comprises a portion of reduced internal diameter, or an internal abutment surface 41, proximal to its rearmost end. As will be described below, the leading portion 42 is moved forwardly in use until the stop 47 hits the internal abutment surface 41, thus preventing further extension of the plunger 40, and causing the trailing portion 48 to also be drawn forwardly along with the leading portion 42.

Figure 6:
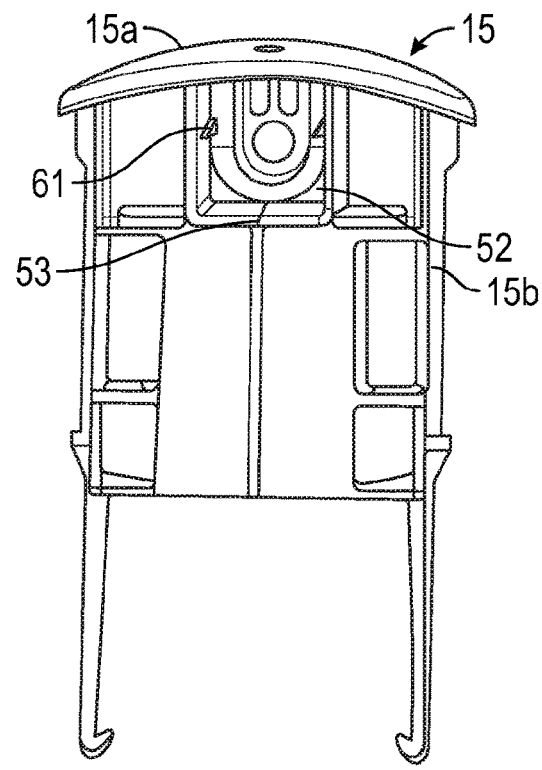
FIG. 6 shows an enlarged view of the trigger with a passageway for receiving the indicator in accordance with the present invention.
Figure 7:
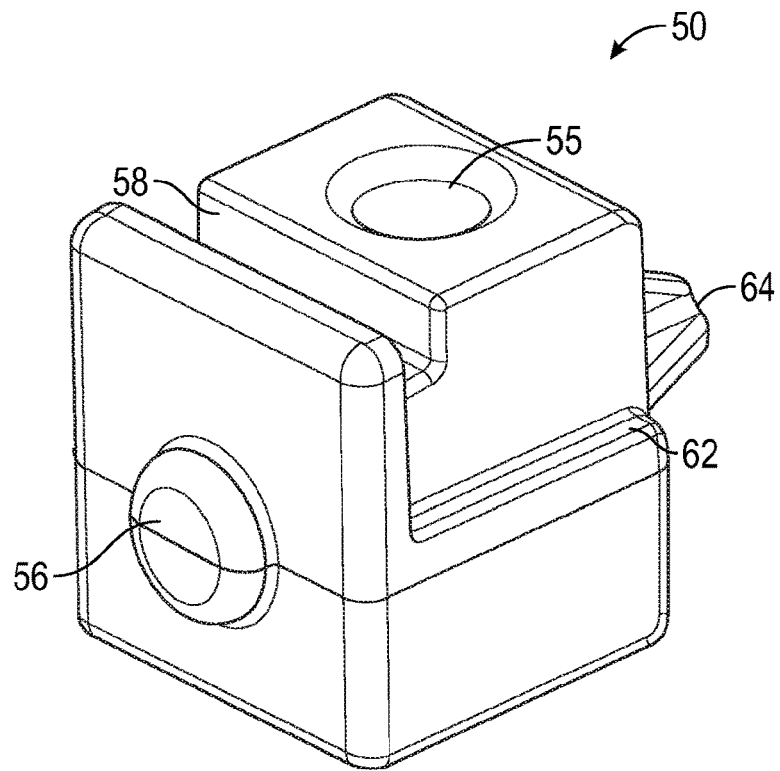
FIG. 7 shows an enlarged view of the indicator for use in the injection device as shown in FIGS. 1-6.

At the rear of the intermediate member 35 there is provided an indicator 50 as shown in FIGS. 3-5. The indicator 50 is formed within the trigger 15 of the injection device 1. As is also shown in FIG. 6, the trigger 15 comprises a body 15b and a cover 15a which together define an inner space within which the indicator 50 is provided. A transverse passageway 52 is defined within the trigger 15 extending substantially across the full width of the trigger 15. A shuttle 54 is slidably received within the passageway 52 and is provided with a spring 51 which is arranged to bias the shuttle 54 towards an indication position at one end of the passageway (the left hand side as shown in the Figs). The spring 51 is received by an extension 64 (shown in FIG. 7), which is provided on the rightmost side of the shuttle 54. An aperture 53 is formed in the forward side of the passageway 52. The rearward end of the trailing portion 48 is received within the aperture 53 when the plunger 40 is in its rearward position. A corresponding aperture 55 is formed in the shuttle 54 within which the trailing portion 48 is also received. In use, the trailing portion 48 locks the shuttle 54 away from the indicating position by holding the spring 51 in a compressed position. It will, however, be appreciated that the trailing portion 48 could alternatively lock the shuttle 54 away from the indicating position if received in front of the shuttle 54, such that an aperture 55 would not be required. The spring 51 is selected to be sufficiently strong that the shuttle 54 strikes the end wall of the transverse channel 52 to create an audible and/or tactile indication.

As shown particularly in FIGS. 3-5 and 7, the cross-section of the shuttle 54 is substantially square in shape, which advantageously may help to keep the shuttle 54 centred within the passageway 52. The leftmost side of the shuttle 54 comprises a striking surface 56 which is substantially curved, or domed, in shape. Advantageously, the curved shape of the striking surface substantially matches the curved shape of the housing 10. In use, the matching shapes may provide a single contact surface, thus allowing a single audible sound or a single tactile sensation to be produced. Otherwise, in cases where the shapes do not match, there is a risk that there may be more than one contact surface and more than one audible sound or more than one tactile sensation could be produced. This may be confusing for the user, who may subsequently struggle to confidently identify when the injection is complete.

The forwardmost end of the aperture 55 comprises a radially inwardly extending portion 57, for example a lip, extending around a portion of the aperture 55, thus giving the aperture 55 an asymmetric profile. In use, the lip 57 aligns with the neck 46 to support the trailing portion 48, and provide an increased resistance, or mechanical coupling, to the forward movement of the trailing portion 48. The rearmost end of the aperture 55 has a larger diameter than the forwardmost end of the aperture 55. Advantageously, this may help in use to prevent the trailing portion 48 from contacting the aperture 55 anywhere other than at the lip 57.

Figure 8:
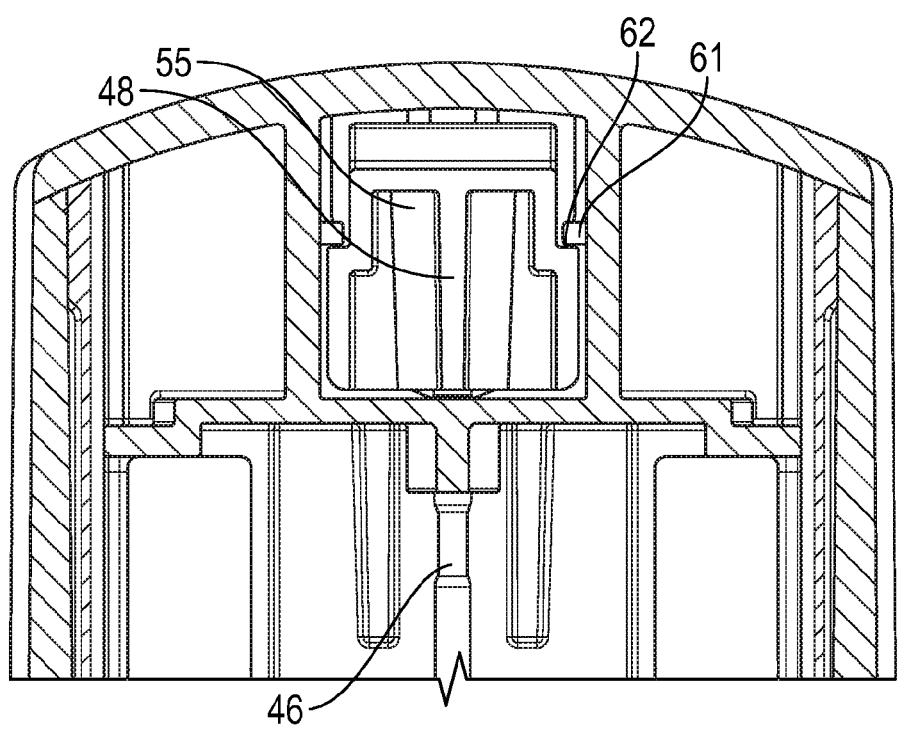
FIG. 8 is an enlarged view of the rear end of the injection device shown in FIG. 1A.

FIGS. 3-5 and 7 particularly show the shuttle 54 further comprising a groove 58 on the rearmost outer surface. The groove 58 is a useful feature during the mechanical assembly of the injection device, as it may help to ensure the shuttle 54 is inserted the right way up. As shown in FIG. 8, the shuttle 54 also comprises an outer stepped face 62 which interacts with a corresponding rib 61 on the inner surface of the passageway 52. This may help to ensure the correct orientation of the shuttle 54 when being manually assembled, such as by hand.

In use, as the first drive spring 32 begins to expand, this results in the forward movement of the intermediate member 35, plunger 40 and indicator 50, as is shown in FIGS. 4-5. The syringe 20 initially moves forward, causing the plunger 40 to press upon the bung or piston 22 of the syringe. However due to the substantially incompressible nature of the medicament contained within the syringe 20, the piston 22 does not move relative to the syringe 20 until the syringe 20 has moved to a forward position and reached a stop.

In use, it may be noted that during initial movement, the plunger 40 is in its collapsed configuration with the trailing portion 48 positioned within the leading portion 42. As the forward movement of the plunger 40 continues under the force of the drive springs 32, 34 the leading portion 42 will begin to move forward of the trailing portion 48. Once the leading portion 42 has slid to its fully extended position relative to the trailing portion 48, the interconnection between the portions 42, 48 requires that the trailing portion 48 also be drawn forwardly along with the leading portion 42. Thus, the portions 42, 48 both extend and move sequentially forward under the force of the drive springs 32, 34 as part of the plunger actuation movement to drive the piston 22 of the syringe 20 fully forward.

The operation of the indicator 50 is illustrated in FIGS. 3-5. FIG. 3 shows the shuttle 54 in its retracted position with the aperture 55 aligned with the aperture 53 of the transverse channel 52. In this position the end of the trailing portion 48 extends through the apertures and latches the shuttle 54. When the injection device 1 is placed against the user's skin, the housing 10 is moved forward, exposing the trigger body 15*b* (not shown). The trigger 15 is then pressed in the forwards direction, thus moving the indicator 50 forward towards the latch 36, and aligning the neck 46 of the trailing portion 48 with the lip 57 of the shuttle aperture 55.

As shown in FIG. 5, the indicator 50 is held against a bias by the trailing portion 48 of the plunger 40. When the plunger 40 reaches the desired forward position (which would typically be as the piston 22 reaches the forward end of the syringe 20 so that a full dose of medicament has been dispensed) the stop 47 hits internal abutment surface 41, and causes trailing portion 48 to move forward of the apertures 53, 55, thus freeing the shuttle 54 to move to its indicating position as shown in FIG. 5. This movement causes the striking surface 56 to contact with the inner surface of the housing 10, and create a kinetic impact which produces an audible and/or tactile indication that the plunger 40 has reached a predetermined forward position.

Although the invention has been described above with reference to the preferred embodiments, it will be appreciated that various changes or modifications may be made without departing from the scope of the invention as defined in the appended claims. In some embodiments the device may be a single use device and, for example, the syringe may be integrally formed with the housing.

Whilst the embodiments described above utilise a kinetic impact to create an indication it will be appreciated that numerous other forms of indication could be used as an additional or alternative indication in response to movement of the trailing portion of the plunger. For example rather than kinetic impact any form of energy could be utilised to create a noise, for example chemical, electrical, fluidic, pneumatic, etc. could all be derived from the motion of the indicator. In some embodiments an electrical signal could be triggered by movement of the plunger to, for example, activate an electronic sounder.

The invention claimed is:

1. An injection device for a delivery of medicament and having an indicator for providing an end of dose indication, the injection device comprising:
 a housing;
 an extendable plunger comprising a leading portion and a trailing portion configured to allow the extendable plunger to extend from an initial length to a maximum extended length, the leading portion and the trailing portion being slidably mounted within the housing;
 an actuation mechanism configured to move the leading portion of the extendable plunger in a forward movement direction relative to a syringe so as to express medicament from the syringe;
 a trigger arrangement moveable in use to release the actuation mechanism; and
 an indicator responsive to the forward movement of the extendable plunger and configured to provide an audible and/or tactile and/or visual indication of an end of a dose when the extendable plunger reaches or approaches its forwardmost position;
 wherein the indicator is biased towards an indicating position and the trailing portion of the extendable plunger is arranged to hold the indicator against the bias;
 the indicator being configured to move in the forward movement direction relative to at least the trailing portion of the extendable plunger in response to an activation movement of the trigger arrangement;
 the trailing portion being arranged to move in the forward movement direction in response to the extendable plunger reaching the maximum extended length; and
 the indicator being arranged to be responsive to the forward movement of the trailing portion.

2. The injection device of claim 1, wherein release of the indicator enables the indicator to move under the bias to create a kinetic impact resulting in the audible and/or tactile indication.

3. The injection device of claim 1, wherein the indicator comprises a resilient member and wherein, in a rearward position of the extendable plunger, the extendable plunger holds the indicator in a stressed position.

4. The injection device of claim 1, wherein the forward movement of the indicator, relative to at least the trailing portion of the extendable plunger, in response to the activation movement of the trigger arrangement increases a mechanical coupling between the indicator and the trailing portion of the extendable plunger holding the indicator in a stressed position.

5. The injection device of claim 1, wherein an aperture of the indicator comprises a radially inwardly extending portion around at least a portion of the aperture, the radially inwardly extending portion being configured to engage the trailing portion in response to activation of the injection device.

6. The injection device of claim 5, wherein the trailing portion comprises a recess for receiving the radially inwardly extending portion proximal to its rearward end.

7. The injection device of claim 6, wherein the recess is defined by a portion of reduced diameter.

8. The injection device of claim 1, wherein the leading portion comprises an internal abutment surface proximal to its rearward end, the trailing portion comprises a portion of increased diameter proximal to its forward end and wherein the portion of increased diameter of the trailing portion is configured to co-operate with the internal abutment surface when the extendable plunger reaches the maximum extended length.

9. The injection device of claim 8, wherein the trailing portion is arranged to move forward in response to the co-operation between the portion of increased diameter of the trailing portion and the internal abutment surface of the leading portion.

10. The injection device of claim 1, wherein the indicator comprises a shuttle disposed in a generally transverse passageway, an indication position of the shuttle being at, or proximal to, an end of the generally transverse passageway and the shuttle being biased towards the indication position along a length of the generally transverse passageway.

11. The injection device of claim 10, wherein the extendable plunger is arranged, in its rearward position, to lock the shuttle against the bias in a position which is spaced away from the end of the generally transverse passageway.

12. The injection device of claim 10, wherein at least a portion of the shuttle comprises a non-circular cross-section when viewed along an axial plane of the injection device.

13. The injection device of claim 10, wherein at least one outer surface of the shuttle comprises a stepped profile, and at least one inner surface of the generally transverse passageway comprises a corresponding rib configured to co-operate with the stepped profile of the shuttle.

14. The injection device of claim 1, wherein the extendable plunger is telescopic.

15. The injection device of claim 1, wherein the actuation mechanism comprises a drive source and a latch arranged to hold the extendable plunger in a rearward position against the drive source and wherein the trigger arrangement comprises a trigger, associated with the housing, and arranged to release the latch to allow the extendable plunger to move forward under an influence of the drive source.

16. The injection device of claim 15, wherein the trigger is further arranged to move the indicator forward relative to at least the trailing portion of the extendable plunger.

17. The injection device as claimed in claim 15, wherein the actuation mechanism further comprises an intermediate drive member and the drive source comprises a first compression drive spring disposed between the intermediate drive member and the housing, or a part associated therewith, and a second compression spring disposed between the intermediate drive member and the extendable plunger.

18. The injection device of claim 15, wherein the leading portion comprises an abutment surface configured to be releasably engaged by the latch.

\* \* \* \* \*